US007351433B2

(12) United States Patent
Yu et al.

(10) Patent No.: US 7,351,433 B2
(45) Date of Patent: Apr. 1, 2008

(54) METHOD FOR PRODUCING POLYMERIC SOL OF CALCIUM PHOSPHATE COMPOUND AND METHOD FOR COATING THE SAME ON A METAL IMPLANT

(75) Inventors: Hyun Seung Yu, Seoul (KR); Dong Soo Lee, Seoul (KR); Kug Sun Hong, Seoul (KR); Choon Ki Lee, Seoul (KR); Jae hyup Lee, Seoul (KR); Dong Ho Lee, Seoul (KR); Bong Soon Chang, Seoul (KR); Jin Young Kim, Seoul (KR); Sung Soo Chung, Gyeonggi-do (KR)

(73) Assignee: Seoul National University Industry Foundation, Seoul (KR)

( * ) Notice: Subject to any disclaimer, the term of this patent is extended or adjusted under 35 U.S.C. 154(b) by 894 days.

(21) Appl. No.: 10/809,509

(22) Filed: Mar. 26, 2004

(65) Prior Publication Data

US 2005/0158399 A1    Jul. 21, 2005

(30) Foreign Application Priority Data

Jan. 20, 2004    (KR) ...................... 10-2004-0004087

(51) Int. Cl.
*A61K 33/42* (2006.01)
*A61L 27/32* (2006.01)
*A61L 33/00* (2006.01)

(52) U.S. Cl. ..................... 424/602; 427/2.27; 427/2.12
(58) Field of Classification Search ................. 424/602; 427/2.27, 2.11, 2.12
See application file for complete search history.

(56) References Cited

U.S. PATENT DOCUMENTS 5,766,669 A * 6/1998 Pugh et al. ................ 427/2.27

| 5,830,480 | A | * | 11/1998 | Ducheyne et al. | .......... 424/400 |
| 5,861,176 | A | * | 1/1999 | Ducheyne et al. | .......... 424/486 |
| 6,416,774 | B1 | * | 7/2002 | Radin et al. | ................ 424/408 |
| 6,426,114 | B1 | * | 7/2002 | Troczynski et al. | ........ 427/2.27 |
| 6,569,489 | B1 | * | 5/2003 | Li | ............................. 427/2.26 |
| 6,667,049 | B2 | * | 12/2003 | Janas et al. | ................. 424/423 |
| 2004/0052861 | A1 | * | 3/2004 | Hatcher et al. | ............. 424/602 |
| 2005/0031704 | A1 | * | 2/2005 | Ahn | ........................... 424/602 |

(Continued)

OTHER PUBLICATIONS

K.A. Gross et al., "Thin Hydroxyapatite Coatings Via Sol-Gel Synthesis", Journal of Materials Science: Materials in Medicine, vol. 9 (1998), pp. 839-843.*

(Continued)

*Primary Examiner*—Sharon E. Kennedy
(74) *Attorney, Agent, or Firm*—Rosenberg, Klein & Lee

(57) ABSTRACT

Disclosed is a method for producing a transparent and homogenized polymeric sol of a calcium phosphate compound, containing apatite and having excellent wettability and bioactivity, according to a sol-gel synthesis, and a method for coating the polymeric sol on a metal implant, in which the polymeric sol is coated on the metal implant and then heat-treated to form a dense coated layer strongly bonded to the metal implant. The polymeric sol is obtained by process of preparing a calcium salt solution, containing calcium ethoxide dissolved in organic acid, and a phosphate solution, containing triethyl phosphite or triethyl phosphate dissolved in the organic acid, mixing the calcium salt solution with the phosphate solution to produce a mixed solution, and aging the mixed solution.

13 Claims, 8 Drawing Sheets

U.S. PATENT DOCUMENTS

2006/0141002 A1* 6/2006 Liu et al. .................... 424/422
2007/0053814 A1* 3/2007 Kobayashi et al. ......... 423/155

OTHER PUBLICATIONS

Dean-Mo Liu, et al., "Water-Based Sol-Gel Synthesis of Hydroxyapatite: Process Development", Biomaterials, vol. 22 (2001), pp. 1721-1730.*

A. Ramila, et al., "Synthesis Routes for Bioactive Sol-Gel Glasses: Alkoxides versus Nitrates", Chemical Materials, vol. 14, No. 2 (2002) pp. 542-548.*

M. J. Filiaggi et al., "Characterization of the Interface in the Plasma-Sprayed HA Coating/Ti-6Al-4V Implant System", Journal of Biomedical Materials Research, vol. 25, Issue 10, pp. 1211-1229, ABSTRACT.*

* cited by examiner

METHOD FOR PRODUCING POLYMERIC SOL OF CALCIUM PHOSPHATE COMPOUND AND METHOD FOR COATING THE SAME ON A METAL IMPLANT

BACKGROUND OF THE INVENTION

1. Field of the Invention

The present invention pertains to a method for producing a polymeric sol of a calcium phosphate compound, containing apatite with excellent bioactivity, according to a sol-gel synthesis, and a method for coating the same on a metal implant, in which the polymeric sol is coated on the metal implant and then heat-treated to form a dense-coated layer strongly bonded to the metal implant. More particularly, the present invention relates to a method for producing a polymeric sol of a calcium phosphate compound, in which the polymeric sol is transparent and homogenized and has excellent wettability because calcium and phosphate components are completely dissolved in the polymeric sol, and a method for coating a calcium phosphate ceramic, containing hydroxyapatite, on a metal implant frequently used in dental and orthopedic surgeries, in which the polymeric sol is coated on the metal implant and then heat-treated to form a dense coated layer strongly bonded to the metal implant.

2. Description of the Related Art

Grafting of a calcium phosphate ceramic, such as hydroxyapatite (HA, $Ca_{10}(PO_4)_6(OH)_2$), tricalcium phosphate (TCP, $Ca_3(PO_4)_2$), tetracalcium phosphate (TTCP, $Ca_4P_2O_9$), and calcium pyrophosphate (CPP, $Ca_2P_2O_7$), into a bone tissue of a rabbit has been conducted by Kitsugi et al., as disclosed in "Biomaterials" 16, 1101-1107 (1995). With respect to this, they observed an interface between the calcium phosphate ceramic and the bone tissue using a transmission electron microscope (TEM), resulting in the finding that the calcium phosphate ceramic was chemically combined with the bone tissue.

The above examples of the calcium phosphate ceramic are all chemically combined with the bone tissue, but different from each other in terms of its dissolution speed in humans. Of them, hydroxyapatite is known as the most stable calcium phosphate ceramic having the most similar chemical properties to inorganic materials constituting the bone tissue of humans in the case of grafting hydroxyapatite into humans. Accordingly, a lot effort has been made in developing a hydroxyapatite ceramic clinically used as an artificial bone material. However, the hydroxyapatite ceramic has relatively high brittleness considered as a disadvantage of a traditional ceramic material even though it has excellent biocompatibility. Hence, an implant made of a metal material, such as stainless steel, cobalt-chromium alloy, and titanium alloy, is frequently used as a structure which must endure a repeating load.

To combine excellent physical strength of a metal material with the high biocompatibility, various studies have been made to coat hydroxyapatite on a surface of the metal implant. The most traditional process of coating hydroxyapatite on the surface of the metal implant is a plasma spray process. According to the plasma spray process, hydroxyapatite powder is moved through a plasma region at 20000 to 30000° C. using a carrier gas to be instantaneously fused, and then bonded to a target substrate. The plasma spray process is more advantageous than the other coating processes, such as a sputtering process and a chemical vapor deposition process, in terms of bond strength. In other words, when the hydroxyapatite powder is bonded to the target substrate according to the plasma spray process, the bond strength of the hydroxyapatite powder to the target substrate is relatively high.

However, when hydroxyapatite particles pass through the very hot plasma region, chemical structures of hydroxyapatite particles are destroyed to release decomposed components, such as tricalcium phosphate, tetracalcium phosphate, calcium oxide, and amorphous calcium pyrophosphate, to enable a coated layer on the target substrate to be absorbed into the body when the coated target substrate is grafted into the body, leading to the dissociation of the coated layer from the target substrate or the reduction of strength of the coated layer (refer to Filiaggi et al. J. Biomed. Mater. Res., 25:1211-1229, 1991).

A sintering temperature of the hydroxyapatite ceramic is 1100° C. or higher, which acts as an obstacle in a developing an improved coating process to avoid the above disadvantages. The metal implant mostly consisting of stainless steel 316 L and titanium ally (Ti-6Al-4V) is largely reduced in terms of the physical strength and is severely oxidized at 1100° C. or higher, and thus, the hydroxyapatite coated layer must be densely sintered at 1000° C. or lower.

Recently, a lot of effort has been made to synthesize the nano-sized hydroxyapatite particles (1 nm=$10^{-9}$ m) to reduce the sintering temperature of the hydroxyapatite ceramic. For example, reference may be primarily made to a sol-gel synthesis, in which metal organics are hydrolyzed to form first particles of three to four nm, and the first particles are subjected to a polycondensation reaction to form gel meshes. When a solvent is removed from the gel meshes, the gel meshes are dried and shrunken, and the shrunken gel meshes are heat-treated to produce final ceramic particles. The sol-gel synthesis is advantageous in that because the ceramic particles are chemically uniform and largely reduced in terms of a size, the ceramic particles have excellent reactivity. However, the sol-gel synthesis is applied to only a special field, such as a coating process, because an amount of the ceramic particles produced according to the sol-gel synthesis is relatively small.

When the hydroxyapatite ceramic produced according to the sol-gel synthesis is coated on an objective body, the hydroxyapatite ceramic is crystallized at relatively low temperatures and its sintering temperature is largely reduced, providing a novel apatite coating process. In this regard, the preferable selection of calcium salts, phosphates, and the solvent is the most important factor in the sol-gel synthesis of the calcium phosphate ceramic. Additionally, in the sol-gel synthesis, it is necessary to ensure a desirable aging condition in which calcium and phosphates are uniformly mixed with each other and sufficiently come into contact with each other.

U.S. Pat. No. 5,766,669 discloses a method of coating an apatite sol on a metal substrate, including mixing calcium nitrate ($Ca(NO_3)_2$) with an ammonium phosphate solution to produce the apatite sol, coating the apatite sol on the metal substrate, and heating the resulting metal substrate at 950 to 1000° C. Furthermore, U.S. Pat. No. 6,569,489 discloses a method of coating apatite on a substrate, including dipping the substrate in an aqueous solution, containing calcium, phosphate, and carbonate ions maintained at 100° C. or lower within a pH range of 6.0 to 7.5 for a sufficiently long time, to chemically react the aqueous solution with the substrate to form a crystalline apatite coated layer on the substrate.

Meanwhile, D. M. Liu et al. attempted the coating of an apatite sol on a pure titanium substrate, in which a solution of calcium nitrate ($Ca(NO_3)_2$) in anhydrous ethanol is mixed with another solution, obtained by adding triethyl phosphite and water into anhydrous ethanol and hydrolyzing the resulting mixture, to produce the apatite sol, as indicated by "Biomaterials" 22 1721-1730 (2001). Additionally, K. A. Gross. et al. suggested a technology of producing of an apatite coated layer, including mixing a first solution of calcium ethoxide in ethanol and ethane diol with a second solution of triethyl phosphite in ethanol and ethane diol to produce an apatite sol, coating the apatite sol on a titanium substrate, and heating the resulting substrate at 800° C., in "J. Mater. Sci. : Mater. In Med. " 9 839-843, (1998).

However, it is undesirable to coat the substrate with the use of an apatite aqueous solution or to use calcium nitrate as the calcium salts because the coated layer with an nonuniform thickness is formed on the substrate due to poor wettability of the apatite sol to the substrate when the apatite aqueous solution is coated on the substrate.

Like in the case of using water as the solvent, in the case of using the mixed solvent of ethanol and ethane diol, the wettability of the apatite sol to the substrate is reduced, preventing the uniform and dense coated layer form being formed on the substrate. Generally, a sol with excellent wettability is very useful to form the coated layer with the uniform thickness because it is uniformly dispersed on a surface of the substrate. Therefore, one of the most important factors in a sol-gel coating method is the wettability of the sol, produced according to the sol-gel synthesis, to the substrate.

A conventional, commercial coating method using the apatite sol has a disadvantage in that it is impossible to form the dense coated layer with the uniform thickness because of the use of the apatite sol with poor wettability. Hence, the coating method using the apatite sol has not been widely utilized even though the coating method is advantageous in that the method is simply conducted and it is not necessary to use costly coating devices.

SUMMARY OF THE INVENTION

Accordingly, the present invention has been made keeping in mind the above problems occurring in the prior art, and an object of the present invention is to provide a method of producing a polymeric sol of a calcium phosphate compound, in which the polymeric sol is transparent and homogenized, and has excellent wettability and bioactivity because calcium and phosphate components are completely dissolved in the polymeric sol.

It is another object of the present invention to provide a method of coating a polymeric sol of a calcium phosphate ceramic, containing hydroxyapatite, on a metal implant frequently used in dental and orthopedic surgeries, in which the polymeric sol is coated on the metal implant and then heat-treated to form a dense coated layer strongly bonded to the metal implant. At this time, the coated layer has a uniform microstructure.

The above and/or other objects are achieved by providing a method for producing a polymeric sol of a calcium phosphate compound containing apatite, which includes preparing a calcium salt solution, containing calcium ethoxide ($Ca(OC_2H_5)_2$) completely dissolved in organic acid, and a phosphate solution, containing triethyl phosphite ($P(OC_2H_5)_3$) or triethyl phosphate ($PO(OC_2H_5)_3$) dissolved in the organic acid, mixing the calcium salt solution with the phosphate solution to produce a mixed solution, and aging the mixed solution. At this time, the organic acid is any one selected from the group consisting of propionic acid ($CH_3CH_2COOH$), acetic acid ($CH_3COOH$), and formic acid ($HCOOH$).

The above and/or other objects are achieved by providing a method for coating a calcium phosphate ceramic on a metal implant according to the present invention. The method includes a first step of coating the polymeric sol on a surface of the metal implant through a dipping, a spinning, or a spraying process, a second step of hydrolyzing a coated layer, including the polymeric sol, on the metal implant at 60 to 100° C., a third step of preheating the hydrolyzed coated layer on the metal implant at 300 to 500° C. to burn organics remaining in the hydrolyzed coated layer, a fourth step of repeating the first to third steps to desirably increase a thickness of the preheated-coated layer, and a fifth step of sintering the resulting metal implant at 500 to 800° C. under a nitrogen atmosphere.

Predetermined calcium salt and phosphate solutions are prepared, mixed with each other, and then aged to produce the polymeric sol containing apatite. According to the present invention, calcium ethoxide powder is added into organic acid, such as propionic acid, acetic acid, and formic acid, so that a molar concentration of calcium ethoxide in the organic acid is 0.005 to 1.0, and then agitated until the calcium ethoxide powder is completely dissolved in the organic acid to produce a calcium salt solution (solution A).

For example, when the molar concentration of the calcium ethoxide powder in the organic acid is less than 0.005, apatite powder is produced in a relatively small amount. On the other hand, when the molar concentration of the calcium ethoxide powder in the organic acid is more than 1.0, the calcium ethoxide powder is insufficiently dissolved in an organic acid solvent. Calcium ethoxide has deliquescence, and thus, calcium ethoxide and the solution A must be treated under a sufficiently dried argon or nitrogen atmosphere.

Meanwhile, triethyl phosphite or triethyl phosphate is added into the organic acid, such as propionic acid, acetic acid, and formic acid, such that a molar ratio of calcium to phosphorus in the calcium phosphate compound is 1 to 2, and then sufficiently agitated to produce a phosphate solution (solution B). Unlike solid calcium ethoxide, triethyl phosphite or triethyl phosphate exists in a liquid phase. Therefore, a separate dissolution process is not required to produce the solution B. With respect to this, triethyl phosphate slowly reacts with calcium salt because a hydrolysis rate of triethyl phosphate is relatively slow. Hence, it takes a long time to produce the apatite, and thus, it is preferable that triethyl phosphite be used as phosphate.

The reason why the molar ratio (Ca/P) of calcium to phosphorus in the calcium phosphate compound is 1.0 to 2.0 is that when the molar ratio (Ca/P) of calcium to phosphorus in the calcium phosphate compound produced by mixing the calcium salt solution (solution A) with the phosphate solution (solution B) deviates from the above molar ratio range, the calcium phosphate compound has poor bioactivity.

When the calcium salt solution (solution A) containing calcium ethoxide completely dissolved therein is mixed with the phosphate solution (solution B) containing triethyl phosphite or triethyl phosphate dissolved therein, the various calcium phosphate compounds may be synthesized according to the molar ratio (Ca/P) of calcium to phosphorus.

In detail, when the molar ratio (Ca/P) of calcium to phosphorus is 1.0, 1.5, 1.67, and 2.0, calcium pyrophosphate ($Ca_2P_2O_7$), tricalcium phosphate ($Ca_3(PO_4)_2$), hydroxyapatite ($Ca_{10}(PO_4)_6(OH)_2$), and tetracalcium phosphate ($Ca_4P_2O_9$) are produced, respectively. In this respect, all of calcium pyrophosphate ($Ca_2P_2O_7$), tricalcium phosphate ($Ca_3(PO_4)_2$), hydroxyapatite ($Ca_{10}(PO_4)_6(OH)_2$), and tetracalcium phosphate ($Ca_4P_2O_9$) have excellent bioactivity.

A mixed solution of the calcium phosphate compound prepared by mixing the calcium salt solution with the phosphate solution is aged at room temperature to 80° C. for a predetermined period to produce a polymeric sol of the calcium phosphate compound. In this regard, an aging time is a maximum of one week at the room temperature, and a maximum of 10 hours at 80° C. When the aging time is longer than one week or 10 hours, the precipitation occurs in the solution, leading to the formation of the nonuniform sol.

The aged sol is transparent, and has a light orange color and excellent wettability.

After the polymeric sol of the calcium phosphate compound having the excellent bioactivity is produced, a metal implant is coated with the polymeric sol according to a dipping, a spinning, or a spraying process, and the sol-coated metal implant is hydrolyzed at 60 to 100° C. The hydrolyzed metal implant is preheated at 300 to 500° C. to burn organics remaining in the coated layer consisting of the polymeric sol. The above procedure is repeated to desirably increase a thickness of the coated layer. The resulting metal implant is then sintered at 500 to 1000° C. under a nitrogen atmosphere.

In this regard, when a sintering temperature of the metal implant is lower than 500° C., the organics are insufficiently burned. On the other hand, when the sintering temperature is higher than 1000° C., physical strength of the metal implant is greatly reduced and the metal implant is severely oxidized.

As described above, in the present invention, when the metal implant is coated with the polymeric sol of the calcium phosphate compound and then heat-treated, the dense coated layer is formed on the metal implant. At this time, bond strength of the polymeric sol to the metal implant is excellent, and the coated layer has a uniform microstructure.

BRIEF DESCRIPTION OF THE DRAWINGS

These and other objects and advantages of the invention will become apparent and more readily appreciated from the following description of the preferred embodiments, taken in conjunction with the accompanying drawings of which.

DETAILED DESCRIPTION OF THE PREFERRED EMBODIMENTS

Figure 1:
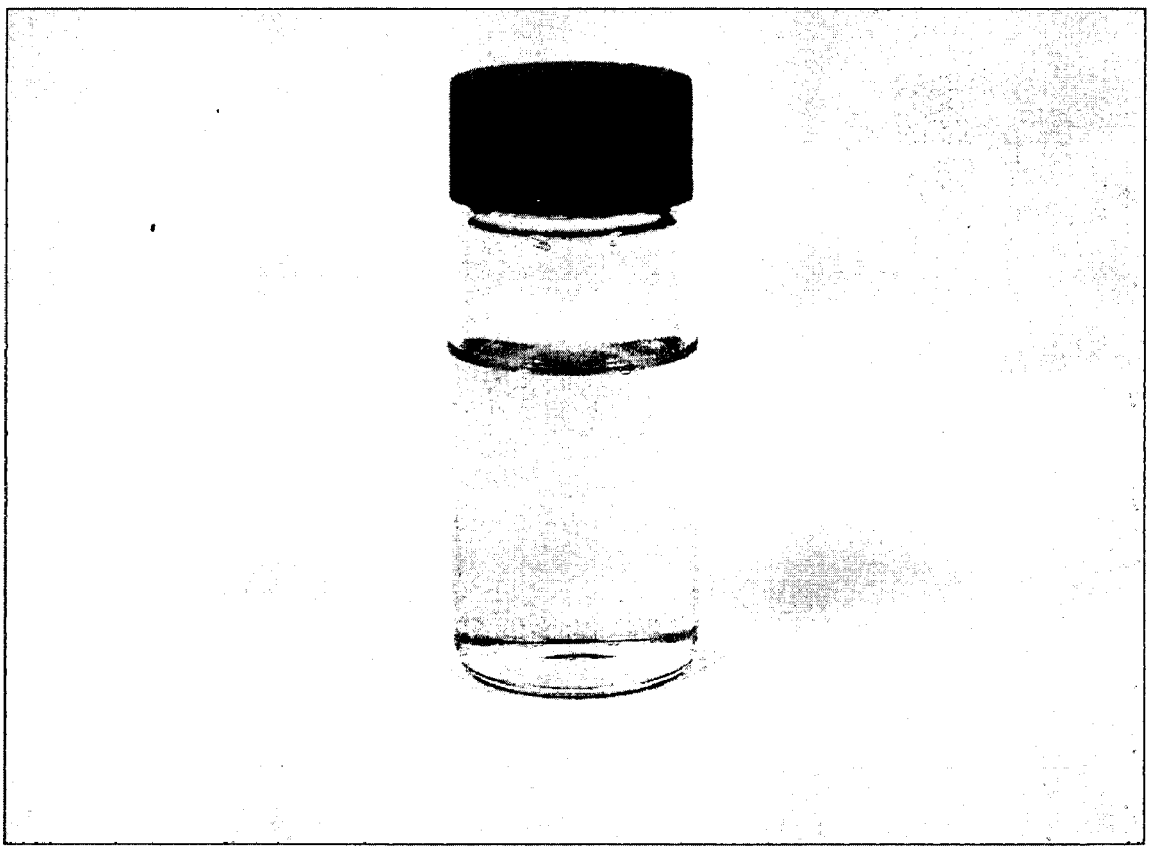
FIG. 1 is a picture showing a transparent and stable apatite sol according to the present invention.

Reference will now be made in detail to the present preferred embodiments of the present invention, examples of which are illustrated in the accompanying drawings, wherein like reference numerals refer to like elements throughout.

With reference to FIG. 1, there is provided a picture showing a transparent and stable apatite sol according to the present invention. According to the present invention, a mixed solution of a calcium phosphate compound is aged at 60° C. for six hours to produce the apatite sol. The apatite sol is transparent and stable, and has a light orange color. The transparency of the apatite sol means that the precipitation does not occur in the apatite sol and the apatite sol is homogeneous. Thereby, when the apatite sol is used as a coating liquid, a coated layer with a uniform thickness is formed on a substrate.

Figure 2:
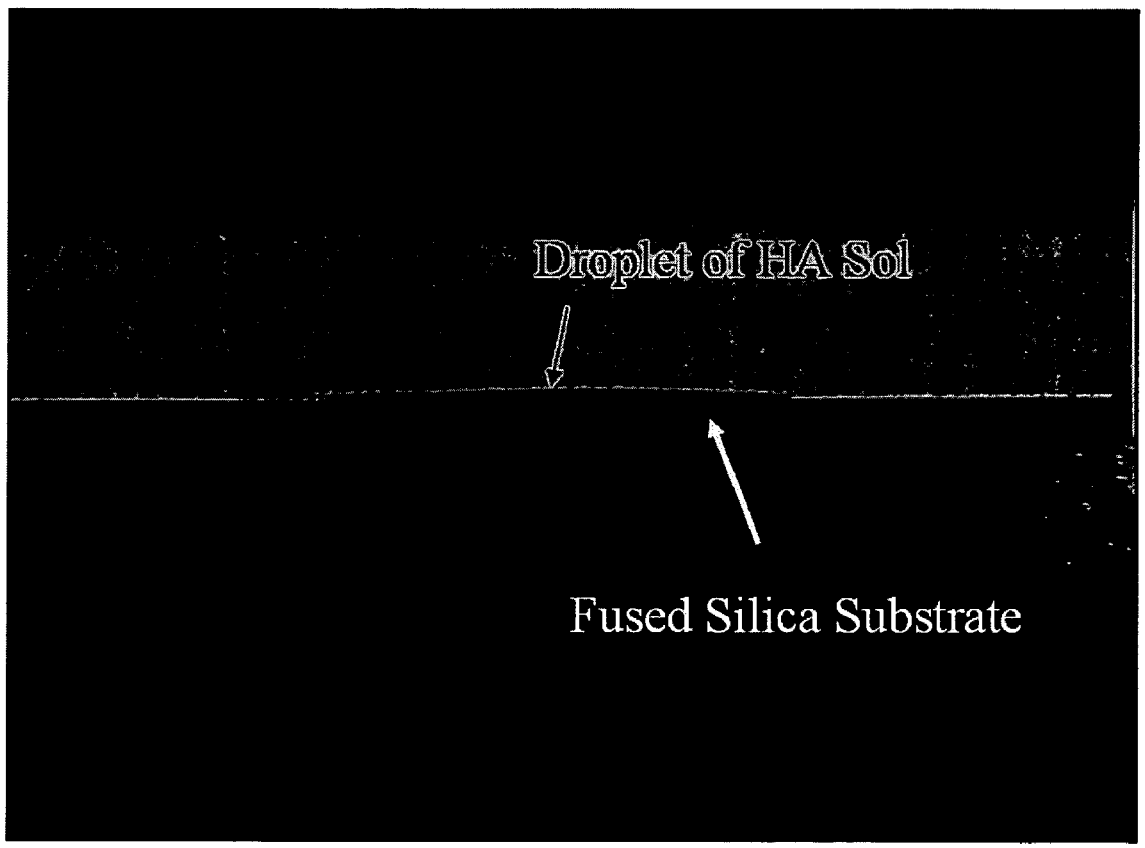
FIG. 2 is a picture showing a section of an amorphous silica substrate, onto which a droplet of the apatite sol is dropped, so as to measure a contact angle between the apatite sol and the silica substrate.

Referring to FIG. 2, there is provided a picture showing a section of an amorphous silica substrate, onto which a droplet of the apatite sol is dropped, so as to measure a contact angle between the apatite sol and the silica substrate. At this time, the apatite sol is produced by aging the mixed solution of the calcium phosphate compound at 60° C. for six hours. Generally, larger contact angel between the apatite sol and the substrate brings about lesser wettability of the apatite sol. As shown in FIG. 2, the apatite sol according to the present invention is uniformly dispersed on the substrate so that the contact angle between the apatite sol and the substrate cannot be measured, thereby ensuring excellent wettability. Additionally, the apatite sol having excellent wettability is useful to be uniformly coated on a subjective body, such as the substrate, and may be useful as a sol for a coating process.

Figure 8:
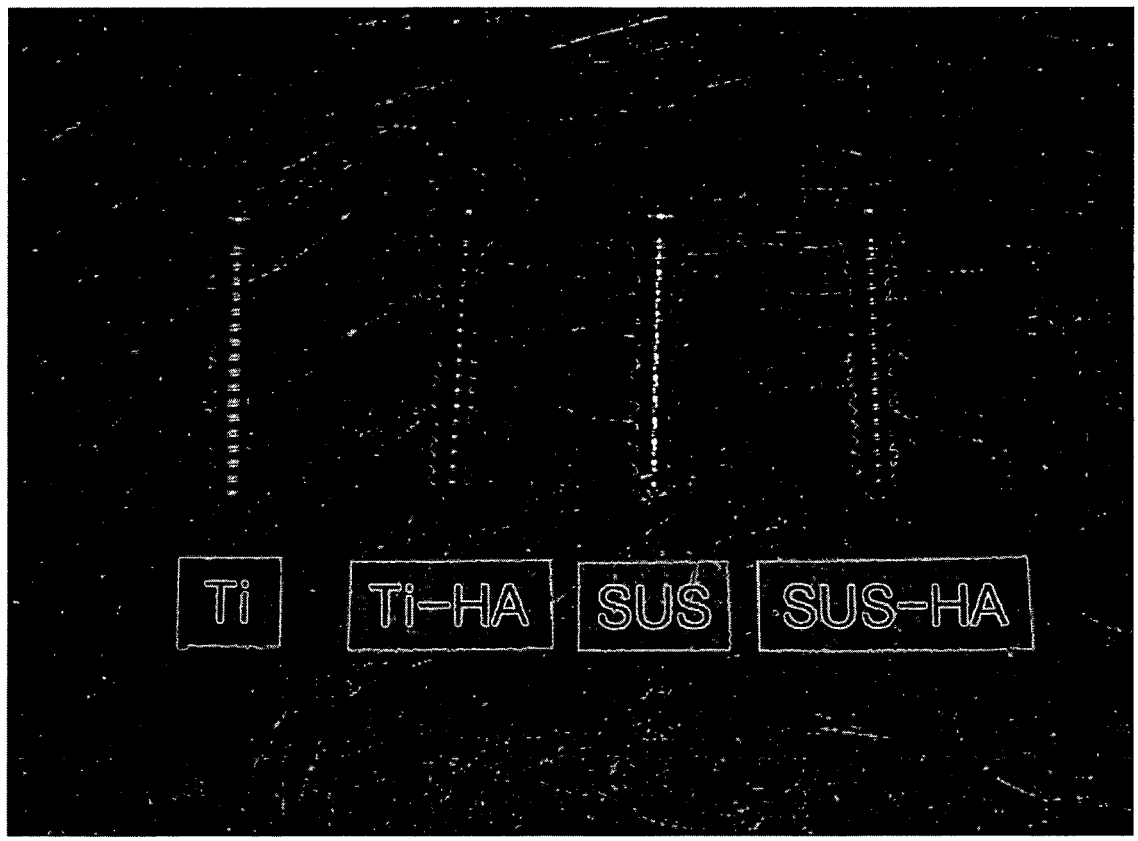
FIG. 8 is a picture showing commercial compact bone screws made of titanium alloy and stainless steel, and apatite-coated screws produced by heat-treating the sol-coated compact bone screws at 700° C. for one hour after the apatite sol is coated on the commercial compact bone screws according to the present invention.

To coat the apatite sol on metal substrates made of stainless steel or titanium alloy, such as various kinds of metal implants frequently used in dental and orthopedic surgeries, for example, on compact bone screws, a pre-rinsed metal implant may be dipped in the aged apatite sol, may be dipped in the aged apatite sol and then subjected to a spinning process, or may be coated with the apatite sol according to the spraying process (refer to FIG. 8).

The sol-coated metal implant is maintained in a drier at 60 to 100° C. for 10 to 15 min to further hydrolyze the coated layer on the metal implant, and then heat-treated in an electric furnace at 300 to 500° C. to burn organics remaining in the coated layer to crystallize the coated layer. This procedure is repeated to increase a thickness of the coated layer to the desired degree. The increase of a heat-treatment temperature leads to the increase of crystallinity of apatite sol and of sizes of particles constituting the coated layer. However, the metal substrate may be oxidized at 500° C. or higher, and thus, the metal substrate must be heat-treated under inert gases, such as nitrogen or argon.

When it is required to produce apatite powder without the coating of the apatite sol on the metal substrate, the apatite sol is heated to 100° C. in a double boiler to completely volatilize a solvent therefrom to produce powder, and the resulting powder is heat-treated at 700 to 1000° C. for two hours under an oxidization atmosphere, thereby accomplishing the apatite powder.

Having generally described this invention, a further understanding can be obtained by reference to examples and comparative examples which are provided herein for purposes of illustration only and are not intended to be limiting unless otherwise specified.

EXAMPLE 1, AND COMPARATIVE EXAMPLES 1 TO 3

Calcium ethoxide was dissolved in 5 cc of propionic acid (example 1), 5 cc of ethanol (comparative example 1), 5 cc of 2-methoxyethanol (comparative example 2), and 5 cc of ethylene glycol (comparative example 3) in a glove box, in which a dried argon gas was charged, to produce a plurality of calcium salt solution (solution A) samples each containing 0.25 M of calcium ethoxide. Additionally, triethyl phosphite was added into 5 cc of propionic acid (example 1), 5 cc of ethanol (comparative example 1), 5 cc of 2-methoxyethanol (comparative example 2), and 5 cc of ethylene glycol (comparative example 3) to produce a plurality of phosphate solution (solution B) samples. At this time, an amount of triethyl phosphite was properly controlled such that a molar ratio of calcium to phosphorus was 1.67 when the solution A samples were mixed with the solution B samples. The solution B samples were then slowly poured into the solution A samples, respectively, and sufficiently agitated for ten minutes. After the completion of agitation, the formation of precipitates in the resulting mixed solutions and wettabilities of the resulting mixed solutions were observed, and the results are described in the following Table 1.

TABLE 1

| | Ex. 1 | Co. Ex. 1 | Co. Ex. 2 | Co. Ex. 3 |
|---|---|---|---|---|
| Calcium salt | Calcium ethoxide | Calcium ethoxide | Calcium ethoxide | Calcium ethoxide |
| Phosphate | Triethyl phosphite | Triethyl phosphite | Triethyl phosphite | Triethyl phosphite |
| Solvent | Propionic acid | Ethanol | 2-methoxy ethanol | Ethylene glycol |
| Conc. of Calcium salt | 0.25 M | 0.25 M | 0.25 M | 0.25 M |
| Reaction temp. | Room temp. | Room temp. | Room temp. | Room temp. |
| Precipitates | None, transparent | Calcium ethoxide is not dissolved | Precipitates are observed | None, transparent |
| Wettability to an amorphous silica substrate | Excellent | Excellent | Excellent | Poor, the resulting solution lumps |
| Suitability for a coating process | Suitable | Unsuitable | Unsuitable | Unsuitable |

As shown in the Table 1, ethanol (comparative example 1), 2-methoxyethanol (comparative example 2), and ethylene glycol (comparative example 3) as well as propionic acid (example 1) were used as the solvent so as to dissolve calcium ethoxide therein. With respect to this, calcium ethoxide was not dissolved in ethanol (comparative example 1), and the precipitates were observed in the case of using 2-methoxyethanol as the solvent (comparative example 2). Further, in the case of using propionic acid (example 1) and ethylene glycol (comparative example 3), the precipitates were not observed and the resulting mixed solutions were transparent.

As for the wettabilities of the resulting mixed solutions to the amorphous silica substrate, the levels of wettability were excellent in the case of using propionic acid (example 1), ethanol (comparative example 1), and 2-methoxyethanol (comparative example 2). However, the level of wettability was poor and the resulting mixed solution lumped in the case of using ethylene glycol (comparative example 3).

Therefore, in consideration of the formation of the precipitates and wettability, propionic acid (example 1) was most suitable for the coating process.

EXAMPLES 2 AND 3

Calcium ethoxide was dissolved in 5 cc of acetic acid (example 2) and 5 cc of formic acid (example 3) in a glove box, in which a dried argon gas was charged, to produce two solution A samples each containing 0.25 M of calcium ethoxide. Additionally, triethyl phosphite was added into 5 cc of acetic acid (example 2) and 5 cc of formic acid (example 3) to produce two solution B samples. At this time, an amount of triethyl phosphite was properly controlled such that a molar ratio of calcium to phosphorus was 1.67 when the solution A samples were mixed with the solution B samples. The solution B samples were then slowly poured into the solution A samples, respectively, and sufficiently agitated for ten minutes. After the completion of agitation, the formation of precipitates in the resulting mixed solutions and wettability of the resulting mixed solutions were observed, and the results are described in the following Table 2.

TABLE 2

| | Example 2 | Example 3 |
|---|---|---|
| Calcium salt | Calcium ethoxide | Calcium ethoxide |
| Phosphate | Triethyl phosphite | Triethyl phosphite |
| Solvent | Acetic acid | Formic acid |
| Conc. of calcium salt | 0.25 M | 0.25 M |
| Reaction temperature | Room temperature | Room temperature |
| Precipitates | None, transparent | None, transparent |
| Wettability to an amorphous silica substrate | Excellent | Excellent |
| Suitability for a coating process | Suitable | Suitable |

The procedure according to example 1 was repeated except that acetic acid (example 2) and formic acid (example 3) were used as the solvent. In the case of using acetic acid (example 2) and formic acid (example 3), the precipitates were not observed and the wettability was excellent, thereby it can be seen that acetic acid and formic acid are suitable for the coating process.

EXAMPLES 4 to 9

Calcium ethoxide was dissolved in 5 cc of propionic acid in a glove box, in which a dried argon gas was charged, to produce a plurality of solution A samples each containing 0.3 M, 0.5 M, 1.0 M, and 1.2 M of calcium ethoxide (examples 4 to 7). Additionally, triethyl phosphite was added into 5 cc of propionic acid to produce a plurality of solution B samples. At this time, an amount of triethyl phosphite was properly controlled such that a molar ratio of calcium to phosphorus was 1.67 when the solution A samples were mixed with the solution B samples. The solution B samples were then slowly poured into the solution A samples, respectively, and sufficiently agitated for ten minutes. After the completion of agitation, the formation of precipitates in the resulting mixed solutions and wettabilities of the resulting mixed solutions were observed, and the results are described in the following Table 3.

TABLE 3

|  | Ex. 4 | Co. Ex. 5 | Co. Ex. 6 | Co. Ex. 7 |
|---|---|---|---|---|
| Calcium salt | Calcium ethoxide | Calcium ethoxide | Calcium ethoxide | Calcium ethoxide |
| Phosphate | Triethyl phosphite | Triethyl phosphite | Triethyl phosphite | Triethyl phosphite |
| Solvent | Propionic acid | Propionic acid | Propionic acid | Propionic acid |
| Conc. of calcium salt | 0.3 M | 0.5 M | 1.0 M | 1.2 M |
| Reaction temp. | Room temp. | Room temp. | Room temp. | Room temp. |
| Dissolution of calcium salt | Completely dissolved | Completely dissolved | A very small amount of precipitates | Precipitates are apparently observed |
| Suitability for a coating process | Suitable | Suitable | Suitable | Unsuitable |

When the concentration of calcium ethoxide in the solvent was changed from 0.3 to 1.2 M according to examples 4 to 7, calcium ethoxide was almost dissolved in the resulting mixed solutions in the cases of 0.3 M, 0.5 M, and 1.0 M of calcium ethoxide (examples 4 to 6). However, in case that the concentration calcium ethoxide was 1.2 M (example 7), the precipitates of calcium ethoxide were apparently observed.

EXAMPLES 10 to 14

Calcium ethoxide was dissolved in 5 cc of propionic acid in a glove box, in which a dried argon gas was charged, to produce a solution A sample containing 0.25 M of calcium ethoxide. Additionally, triethyl phosphite was added into 5 cc of propionic acid to produce a solution B sample. At this time, an amount of triethyl phosphite was properly controlled such that a molar ratio of calcium to phosphorus was 1.67 when the solution A sample was mixed with the solution B sample. The solution B sample was then slowly poured into the solution A sample, and sufficiently agitated at room temperature for ten minutes.

The resulting mixed solutions were heated from the room temperature to target temperatures (room temperature, 40° C., 60° C., 80° C., and 90° C.: examples 10 to 14) in ten minutes, and then aged at the target temperatures. The formation of precipitates in the resulting mixed solutions was observed, and the results are described in the following Table 4.

TABLE 4

|  | Ex. 10 | Ex. 11 | Ex. 12 | Ex. 13 | Ex. 14 |
|---|---|---|---|---|---|
| Calcium salt | Calcium ethoxide | Calcium ethoxide | Calcium ethoxide | Calcium ethoxide | Calcium ethoxide |
| Phosphate | Triethyl phosphite | Triethyl phosphite | Triethyl phosphite | Triethyl phosphite | Triethyl phosphite |
| Solvent | Propionic acid | Propionic acid | Propionic acid | Propionic acid | Propionic acid |
| Conc. of calcium salt | 0.25M | 0.25M | 0.25M | 0.25M | 0.25M |
| Aging temp. | Room temp. | 40° C. | 60° C. | 80° C. | 90° C. |
| Time for forming precipitates | After 9 days | After 24 hours | After 16 hours | After 12 hours | After 3 hours |

As shown in the Table 4, in case that the resulting mixed solutions were aged at the room temperature, 40° C., 60° C., 80° C., and 90° C. (examples 10 to 14), the time required to form the precipitates was shortened in proportion to the aging temperature. Furthermore, when the resulting mixed solution was aged at 90° C., the precipitates were observed after three hours, which was an insufficient time for a coating process.

EXAMPLES 15 to 18

Calcium ethoxide was dissolved in 5 cc of propionic acid in a glove box, in which a dried argon gas was charged, to produce a solution A sample containing 0.25 M of calcium ethoxide. Additionally, triethyl phosphite was added into 5 cc of propionic acid to produce a plurality of solution B samples. At this time, amounts of triethyl phosphite, added to propionic acid, were properly controlled such that molar ratios of calcium to phosphorus (Ca/P) were 1.0, 1.5, 1.67, and 2.0 (examples 15 to 18) when the solution A sample was mixed with the solution B samples. Each of the solution B samples were then slowly poured into the solution A sample, and sufficiently agitated at room temperature for ten minutes.

The resulting mixed solutions were heated from the room temperature to 120° C. in ten minutes to completely remove solvents from the resulting mixed solutions to produce a plurality of powder samples, and the powder samples thusly produced were heat-treated at 1000° C. for four hours. The resulting powder samples were confirmed by use of an X-ray diffractometer, and the results are described in the following Table 5.

TABLE 5

|  | Ex. 15 | Ex. 16 | Ex. 17 | Ex. 18 |
|---|---|---|---|---|
| Calcium salt | Calcium ethoxide | Calcium ethoxide | Calcium ethoxide | Calcium ethoxide |
| Phosphate | Triethyl phosphite | Triethyl phosphite | Triethyl phosphite | Triethyl phosphite |
| Solvent | Propionic acid | Propionic acid | Propionic acid | Propionic acid |
| Conc. of calcium salt | 0.25 M | 0.25 M | 0.25 M | 0.25 M |
| Conc. of phosphate | 0.25 M | 0.16 M | 0.15 M | 0.125 M |

TABLE 5-continued

| | Ex. 15 | Ex. 16 | Ex. 17 | Ex. 18 |
|---|---|---|---|---|
| [1]Crystal | Beta-type calcium pyrophosphate ($\beta$-Ca$_2$P$_2$O$_7$) | Beta-type tricalcium phosphate ($\beta$-Ca$_3$(PO$_4$)$_2$) | Hydroxyapatite (Ca$_{10}$(PO$_4$)$_6$(OH)$_2$) | Hydroxyapatite(Ca$_{10}$(PO$_4$)$_6$(OH)$_2$), calcium oxide (CaO) mixture (tetracalcium phosphate (Ca$_4$P$_2$O$_9$) is confirmed after the heat-treatment of dried powder at 1000° C. for 4 hours) |

[1]Crystal: a crystal of the dried powder heat-treated at 1000° C. for 4 hours

As described above, after the resulting mixed solutions having the molar ratios of calcium to phosphorus of 1.0, 1.5, 1.67, and 2.0 (examples 15 to 18) were produced, the solvents were removed from the resulting mixed solutions to produce the powder samples. At this time, the powder samples were heat-treated. Through an analysis of the heat-treated powder samples, it can be seen that beta-type calcium pyrophosphate ($\beta$-Ca$_2$P$_2$O$_7$), beta-type tricalcium phosphate ($\beta$-Ca$_3$(PO$_4$)$_2$), hydroxyapatite (Ca$_{10}$(PO$_4$)$_6$(OH)$_2$), and tetracalcium phosphate (Ca$_4$P$_2$O$_9$) are obtained in the cases of the molar ratios (Ca/P) of 1.0 (example 15), 1.5 (example 16), 1.67 (example 17), and 2.0 (example 18), respectively.

EXAMPLE 19

Calcium ethoxide was dissolved in 5 cc of propionic acid in a glove box, in which a dried argon gas was charged, to produce a solution A sample containing 0.25 M of calcium ethoxide. Additionally, triethyl phosphite was added into 5 cc of propionic acid to produce a solution B sample. At this time, an amount of triethyl phosphite, added to propionic acid, was properly controlled such that a molar ratio of calcium to phosphorus (Ca/P) was 1.67 when the solution A sample was mixed with the solution B sample. The solution B sample was then slowly poured into the solution A sample, and sufficiently agitated for ten minutes to produce a sol solution. The sol solution was heated to 60° C. and then maintained at 60° C. for six hours to be aged. After six hours, the aged sol was cooled at room temperature, thereby accomplishing the resulting coating sol.

An amorphous silica substrate rinsed with an acetone solution was dipped in the apatite coating sol and then drawn from the apatite coating sol to be coated with the apatite coating sol. The coated silica substrate was left in a drier at 100° C. for ten minutes to hydrolyze a coated layer, consisting of the apatite coating sol, on the silica substrate. The dried silica substrate was maintained in an electric furnace at 500° C. for 15 minutes to burn organics remaining in the coated layer to crystallize the coated layer into apatite. This procedure was repeated five times to accomplish the resulting silica substrate. The coated layer of the resulting silica substrate was observed, and the results are described in the following Table 6.

COMPARATIVE EXAMPLE 4

After an apatite coating sol was prepared according to the same procedure as example 19, an amorphous silica substrate rinsed with an acetone solution was dipped in the apatite coating sol and then drawn from the apatite coating sol, thereby being coated with the apatite coating sol. The coated silica substrate was left in a drier at 100° C. for ten minutes to hydrolyze a coated layer, consisting of the apatite coating sol, on the silica substrate. The coating of the silica substrate with the apatite coating sol was repeated five times. The silica substrate was then maintained in an electric furnace at 500° C. for 15 minutes to accomplishing the resulting silica substrate. The coated layer of the resulting silica substrate was observed with the naked eye, and the results are described in the following Table 6.

TABLE 6

| | | Comparative example 4 | Example 19 |
|---|---|---|---|
| Preparation condition of the coating sol | Calcium salt | Calcium ethoxide | Calcium ethoxide |
| | Phosphate | Triethyl phosphite | Triethyl phosphite |
| | Solvent | Propionic acid | Propionic acid |
| | Conc. of calcium salt | 0.25 M | 0.25 M |
| | Aging temp. | 60° C. | 60° C. |
| | Aging time | 6 hours | 6 hours |
| Coating condition | Hydrolysis | Hydrolyzed at 100° C. for 10 min | Hydrolyzed at 100° C. for 10 min |
| | Coating procedure | After the coating and hydrolysis are repeated five times, the coated layer is maintained at 500° C. for 15 min | The coating, hydrolysis, and maintaining of the coated layer at 500° C. for 15 min are repeated five times |
| | State of the coated layer | A portion of the coated layer peels off, and the nonuniform coated layer | The transparent and uniform coated layer |

In case that a procedure of coating the apatite coating sol on the silica substrate, hydrolyzing the coated layer, and maintaining the hydrolyzed coated layer at 500° C. for 15 min was repeated five times as described in example 19, the transparent and uniform coated layer was formed on the silica substrate. However, when the coated layer was maintained at 500° C. for 15 min after the coating and hydrolysis of the apatite coating sol were repeated five times, a portion of the coated layer peeled off, and the nonuniform coated layer was formed on the silica substrate.

Figure 3:
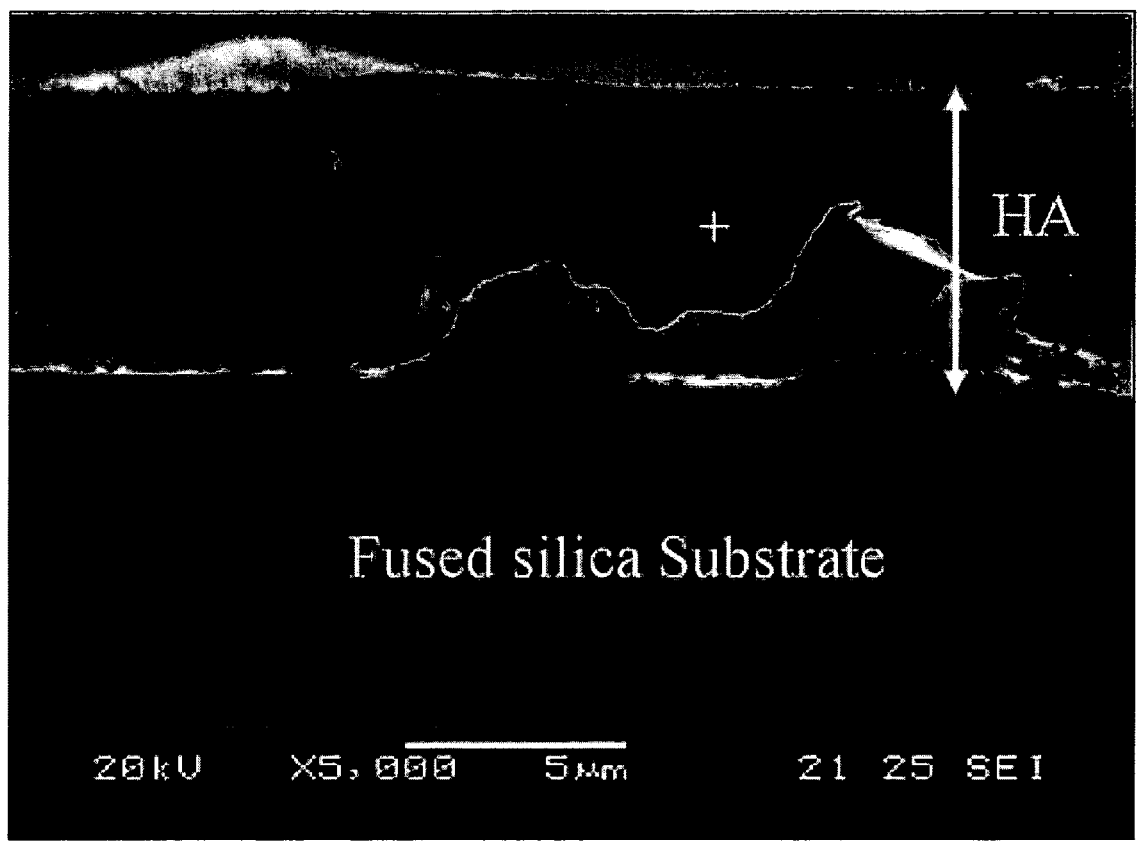
FIG. 3 is a scanning electron microscope (SEM) picture showing a section of an apatite-coated layer on the amorphous silica substrate.

Thereafter, the apatite-coated substrate was heated from 600 to 800° C. at a heating rate of 5° C./min and then maintained at 800° C. for one hour to increase crystallinity of the apatite-coated layer and sizes of particles constituting the coated layer, thereby completing the heat-treatment of the apatite-coated substrate. The heat-treated substrate was cooled at a cooling rate of 5° C./min. With reference to FIG. 3, there is provided a SEM picture showing a section of the apatite-coated layer on the amorphous silica substrate so as to measure a thickness of the apatite-coated layer. Through FIG. 3, it was confirmed that the thickness of the apatite-coated layer was about 5 μm.

Figure 4:
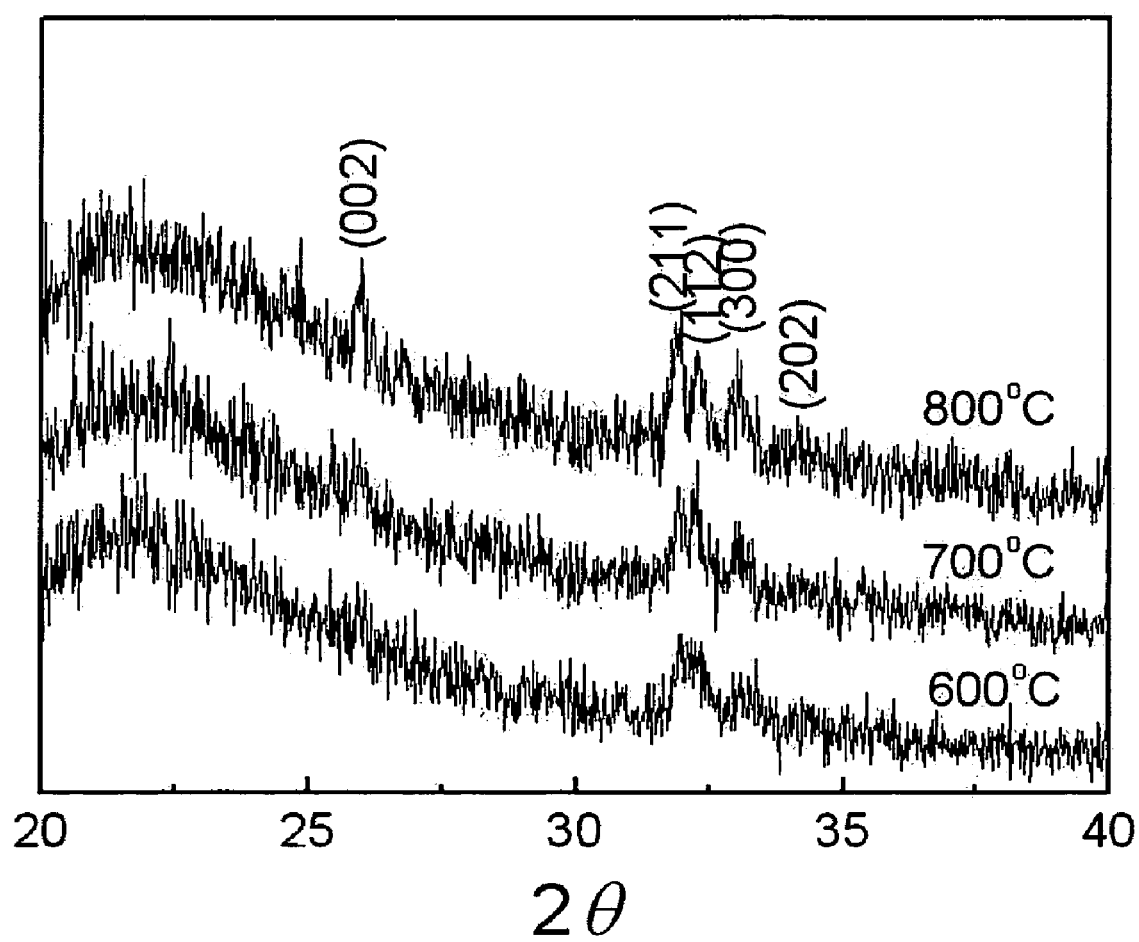
FIG. 4 is an X-ray diffraction graph of the coated layer of the apatite-coated substrate heat-treated at 600 to 800° C. for one hour.

FIG. 4 is an X-ray diffraction graph of the coated layer of the apatite-coated substrate heat-treated at 600 to 800° C. for one hour to confirm components constituting the coated layer. At this time, the apatite-coated substrate was scanned at a speed of 5°/min in a range of 2Θ 20° to 40°. As shown in FIG. 4, a hydroxyapatite diffraction peak was observed for the substrate heat-treated at 600° C. Furthermore, the hydroxyapatite diffraction peak was divided into several peaks according to the increase of a temperature of the heat-treatment ranging from 700 to 800° C., which means the increase of the crystallinity of the coated layer.

Figure 5:
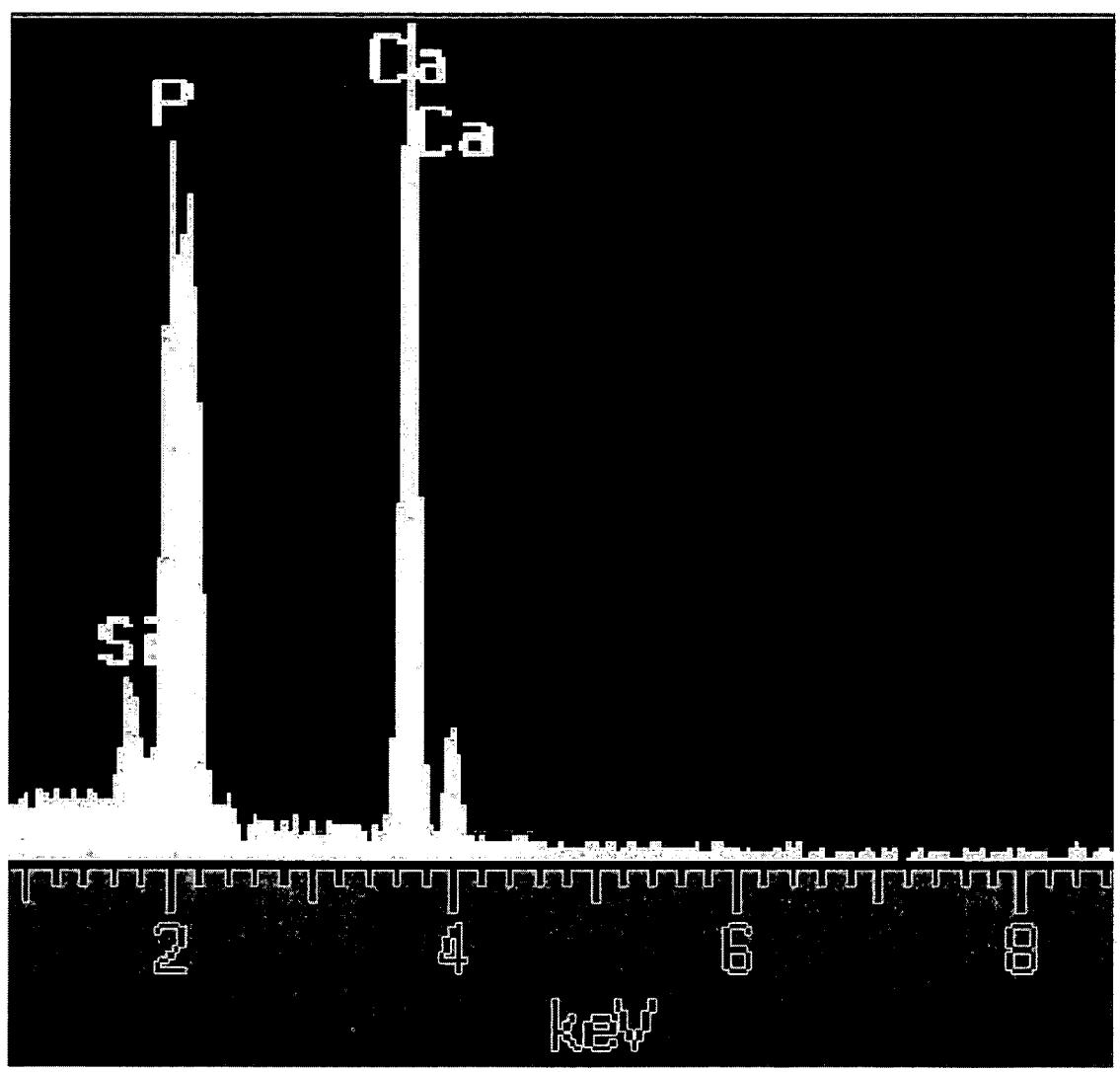
FIG. 5 is a spectrum of the apatite-coated layer analyzed using an energy dispersive X-ray spectroscopy (EDS) to confirm components constituting the apatite-coated layer.

FIG. 5 is a spectrum of the apatite-coated layer analyzed using an EDS, installed in the SEM, to confirm components constituting the apatite-coated layer. With respect to this, a lot amount of calcium and phosphorus were detected, and a small amount of Si constituting the substrate was detected. Accordingly, it was confirmed that the apatite-coated layer was composed of hydroxyapatite including calcium and phosphorus.

Figure 6:
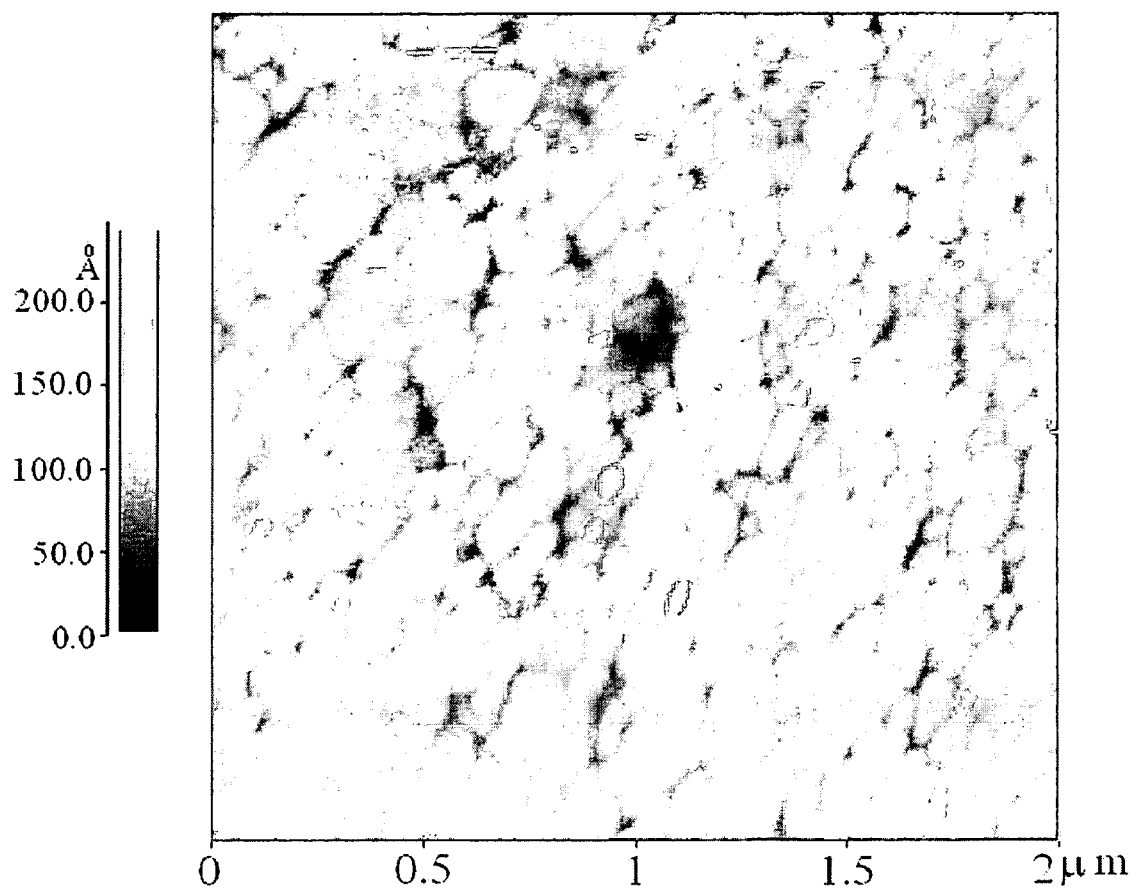
FIGS. 6 and 7 are atomic force microscopy images showing a microstructure and a surface roughness of the apatite-coated layer heat-treated at 700° C. for one hour, respectively.
Figure 7:
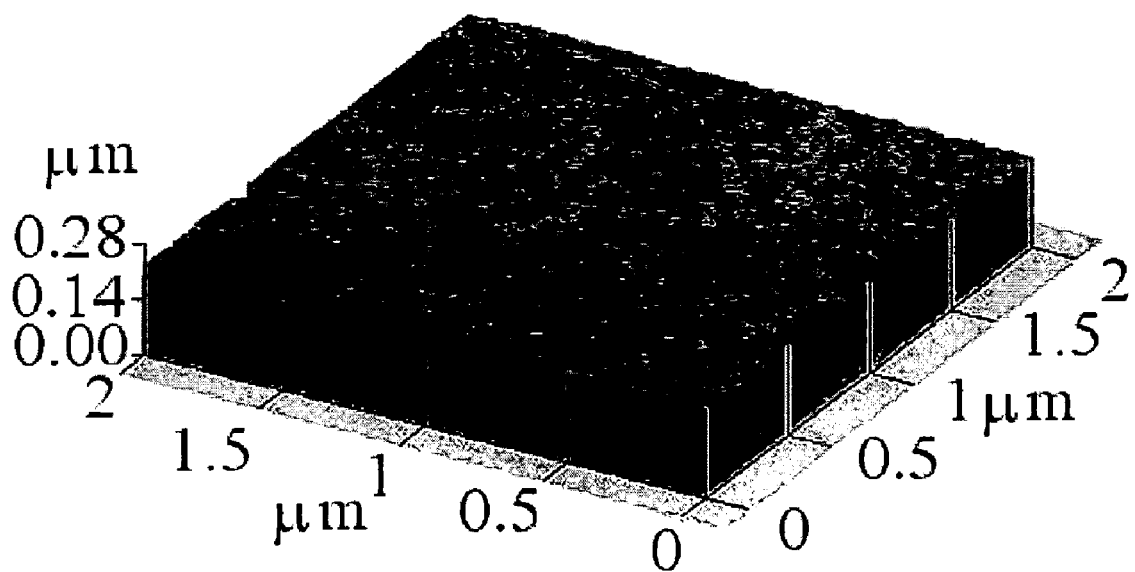

FIGS. 6 and 7 are atomic force microscopy images showing a microstructure and a surface roughness of the apatite-coated layer heat-treated at 700° C. for one hour, respectively. Referring to FIG. 6, apatite particles with a size of 50 to 100 nm are densely formed, and the apatite-coated layer is scarcely irregular and has a uniform thickness as shown in FIG. 7.

Meanwhile, bond strength of the apatite-coated layer to the substrate was estimated using a scratch tester, resulting in that the coated layer started to peel off when a probe needle was applied in a force of 25 N to the coated layer. Generally, because the bond strength of a ceramic coated layer to a cutting tool is about 30 N, the apatite-coated layer according to the present invention may be usefully applied to a medical field.

FIG. 8 is a picture showing commercial compact bone screws (Ti, SUS), made of titanium alloy (Ti-6Al-4V) and stainless steel (SUS 316L), clinically used in the medical field, and apatite-coated screws (Ti-HA, SUS-HA), produced by heat-treating the sol-coated compact bone screws at 700° C. for one hour after the hydroxyapatite sol (HA) is coated on the commercial compact bone screws according to the present invention. As shown in FIG. 8, coated-layers of the apatite-coated screws are transparent and dense. Therefore, it can be seen that metal implants clinically used in the medical field are easily coated with the sol according to the present invention.

As apparent from the above description, the present invention provides a method of producing a polymeric sol of a calcium phosphate compound, in which the polymeric sol is transparent and homogenized and has excellent wettability because calcium and phosphate components are completely dissolved in the polymeric sol, and a method of coating a polymeric sol of a calcium phosphate ceramic on a metal implant frequently used in dental and orthopedic surgeries, in which the polymeric sol is coated on the metal implant and then heat-treated to form a dense coated layer strongly bonded to the metal implant. At this time, the coated layer has a uniform microstructure.

Therefore, the present invention is advantageous in that the calcium phosphate ceramic containing apatite with excellent bioactivity is densely coated on the metal implant in a desired thickness.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for producing a polymeric sol of a calcium phosphate compound, comprising:
   preparing a calcium salt solution, containing calcium ethoxide dissolved in organic acid, and a phosphate solution, containing triethyl phosphite or triethyl phosphate dissolved in the organic acid; and
   mixing the calcium salt solution with the phosphate solution to produce a mixed solution, and aging the mixed solution.

2. The method as set forth in claim 1, wherein the organic acid is at least one selected from the group consisting of propionic acid, acetic acid, and formic acid.

3. The method as set forth in claim 1, wherein the calcium ethoxide is dissolved in the organic acid such that a molar concentration of the calcium ethoxide in the organic acid is 0.005 to 1.0.

4. The method as set forth in claim 1, wherein the triethyl phosphite or triethyl phosphate is dissolved in the organic acid such that a molar ratio of calcium to phosphorus in the calcium phosphate compound is 1.0 to 2.0.

5. The method as set forth in claim 4, wherein the calcium phosphate compound is any one selected from the group consisting of hydroxyapatite, tricalcium phosphate, tetracalcium phosphate, and calcium pyrophosphate.

6. The method as set forth in claim 1, wherein the mixed solution is aged at room temperature for a maximum of one week, or at 80° C. for a maximum of ten hours.

7. A method for coating a calcium phosphate ceramic on a metal implant, comprising:
   a first step of preparing a calcium salt solution, containing calcium ethoxide dissolved in organic acid, and a phosphate solution, containing triethyl phosphite or triethyl phosphate dissolved in the organic acid;
   a second step of mixing the calcium salt solution with the phosphate solution to produce a mixed solution, and aging the mixed solution at room temperature for a maximum of one week or at 80° C. for a maximum of ten hours to produce a polymeric sol of a calcium phosphate compound;

a third step of coating the polymeric sol on a surface of the metal implant;

a fourth step of hydrolyzing a coated layer, including the polymeric sol, on the metal implant;

a fifth step of preheating the hydrolyzed coated layer on the metal implant to burn organics remaining in the hydrolyzed coated layer;

a sixth step of repeating the first to fifth steps to desirably increase a thickness of the preheated-coated layer; and a seventh step of sintering the resulting metal implant at 500 to 800° C. under a nitrogen atmosphere.

8. The method as set forth in claim 7, wherein the organic acid is at least one selected from the group consisting of propionic acid, acetic acid, and formic acid.

9. The method as set forth in claim 7, wherein the calcium ethoxide is dissolved in the organic acid such that a molar concentration of the-calcium ethoxide in the organic acid is 0.005 to 1.0

10. The method as set forth in claim 7, wherein the triethyl phosphite or triethyl phosphate is dissolved in the organic acid such that a molar ratio of calcium to phosphorus in the calcium phosphate compound is 1.0 to 2.0.

11. The method as set forth in claim 7, wherein the coating of the polymeric sol is conducted through a dipping, a spinning, or a spraying process.

12. The method as set forth in claim 7, wherein the hydrolyzing of the coated layer is conducted at 60 to 100° C.

13. The method as set forth in claim 7, wherein the preheating of the hydrolyzed coated layer is conducted at 300 to 500° C.

* * * * *